United States Patent [19]

Kay

[11] 4,013,447
[45] Mar. 22, 1977

[54] COMPOSITIONS CONTAINING HERBICIDAL THIATRIAZINONE DERIVATIVES AND USE THEREOF

[75] Inventor: Ian Trevor Kay, Wokingham, England

[73] Assignee: Imperial Chemical Industries Limited, London, England

[22] Filed: Feb. 20, 1975

[21] Appl. No.: 551,290

[30] Foreign Application Priority Data

Mar. 1, 1974 United Kingdom ............ 9317/74

[52] U.S. Cl. .................. 71/91; 260/243 R; 260/293.88; 260/326.86; 260/454; 260/481 C; 260/482 C; 260/564 E; 424/246
[51] Int. Cl.² .......................... A01N 9/12
[58] Field of Search ............ 71/91; 260/243 R; 424/246

[56] References Cited

UNITED STATES PATENTS

| | | | |
|---|---|---|---|
| 3,270,027 | 8/1966 | Surrey | 71/91 |
| 3,407,197 | 10/1968 | Wright | 71/91 |
| 3,544,570 | 12/1970 | Timmler et al. | 71/93 |
| 3,711,475 | 1/1973 | Disselkotter | 71/91 |
| 3,817,993 | 6/1974 | Franke | 260/243 R |

OTHER PUBLICATIONS

Disselkotter, "2,3-Dihydro-4H-1,2,4,6 etc.," (1971) CA 74 No. 125740a. (1971).

*Primary Examiner*—Glennon H. Hollrah
*Attorney, Agent, or Firm*—Cushman, Darby & Cushman

[57] ABSTRACT

A process of severely damaging or killing unwanted plants, which comprises applying to the locus area, an effective amount of a thiatriazine compound of the formula

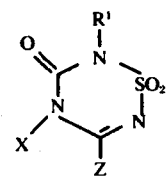

and salts thereof, wherein $R^1$ is cyclohexyl or an alkyl radical; X is a hydrogen atom or an alkyl group of 1 to 3 carbon atoms; and Z is a group $R^2S-$ wherein $R^2$ is an alkyl group of 1 to 4 carbon atoms, or Z is a group $-NR^3R^4$ wherein $R^3$ is a hydrogen atom, an alkyl radical of 1 to 5 carbon atoms, or an alkanoyl radical of 2 to 5 carbon atoms, and $R^4$ is an alkyl radical of 1 to 5 carbon atoms.

8 Claims, No Drawings

COMPOSITIONS CONTAINING HERBICIDAL THIATRIAZINONE DERIVATIVES AND USE THEREOF

This invention relates to 1,2,4,6-thiatriazine derivatives having herbicidal and fungicidal properties, and to herbicidal compositions and processes utilising such thiatriazine derivatives.

According to the present invention there are provided thiatriazine derivatives of the formula:

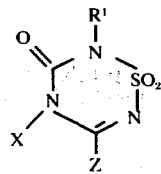

and salts thereof, wherein R represents an aliphatic or alicyclic radical; X represents a hydrogen atom or an aliphatic radical; and Z represents a group $R^2S$— wherein $R^2$ represents an aliphatic radical, or Z is an amino group —$NR^3R^4$ wherein $R^3$ represents a hydrogen atom, an aliphatic radical, or a carboxylic acyl radical, and $R^4$ represents an aliphatic radical, or wherein $R^3$ and $R^4$ together with the nitrogen atom to which they are attached, form a five or six membered heterocyclic ring.

Preferred compounds according to the invention include those in which the group $R^1$ is an alkyl radical of from 1 to 8 carbon atoms and more particularly 2 to 4 carbon atoms. Particularly preferred compounds include those in which the carbon atom of $R^1$ which is attached to the ring nitrogen is a secondary or tertiary carbon atom, that is to say, a carbon atom which is itself linked to two or three other carbon atoms respectively. Examples of such compounds include those in which $R^1$ is an isopropyl, 2-butyl, tertiary butyl, or cyclohexyl radical.

The group X is preferably an alkyl group of from 1 to 3 carbon atoms, for example a methyl group.

The group $R^2$ is preferably an alkyl or alkenyl group of from 1 to 4 carbon atoms, for example a methyl group. When $R^3$ represents an aliphatic radical, it is preferably an alkyl radical of from 1 to 5 carbon atoms, for example a methyl or ethyl radical. When $R^3$ is a carboxylic acyl radical, it is preferably an alkanoyl radical of from 2 to 5 carbon atoms, for example an acetyl radical. The group $R^4$ is preferably an alkyl radical of 1 to 5 carbon atoms. When $R^3$ and $R^4$, together with the nitrogen atom to which they are attached, form a 5- or 6-membered heterocyclic ring, the ring is preferably a pyrrolidine or piperidine ring. When the group X is a hydrogen atom, the compounds of the invention are acidic, and will form salts with bases. Salts can be prepared by conventional methods from, for example, alkali metal hydroxides, for example sodium or potassium hydroxide. Salts may also be prepared from alkaline earth metal hydroxides, for example calcium and magnesium hydroxides; from ammonia; and from organic amines, for example from primary, secondary and tertiary aliphatic amines, particularly such amines wherein the one, two, or three aliphatic groups contain from 1 to 6 carbon atoms.

Examples of compounds according to the invention are listed in Table 1 below.

TABLE 1

| Compound No. | $R^1$ | X | Z | Melting Point °C |
|---|---|---|---|---|
| 1 | $CH_3$ | H | $-N(CH_3)_2$ | 275-276 |
| 2 | n $C_4H_9$ | H | $-N(CH_3)_2$ | 196 |
| 3 | cyclo hexyl | H | $-N(CH_3)_2$ | 260-262 |
| 4 | n $C_4H_9$ | H | $-N(C_2H_5)_2$ | 142 |
| 5 | iso $C_3H_7$ | H | $-N(CH_3)_2$ | 256 |
| 6 | iso $C_3H_7$ | $CH_3$ | $-N(CH_3)_2$ | 95 |
| 7 | iso $C_3H_7$ | $CH_3$ | $-NHCH_3$ | 156-157 |
| 8 | $CH_3$ | $CH_3$ | $-NHCH_3$ | 184-185 |
| 9 | $CH_3$ | $CH_3$ | $-N(CH_3)_2$ | 104-106 |
| 10 | sec $C_4H_9$ | H | $-NHCH_3$ | 134-137 |
| 11 | sec $C_4H_9$ | $CH_3$ | $-NHCH_3$ | 135-136 |
| 12 | sec $C4H_9$ | H | $-N(CH_3)_2$ | 177-178 |
| 13 | sec $C_4H_9$ | $CH_3$ | $-N(CH_3)_2$ | 79-80 |
| 14 | sec $C_4H_9$ | H | $-N(COCH_3)(C_3H_7\text{-}n)$ | 87-88 |
| 15 | iso $C_3H_7$ | H | $-NH$ neo $C_5H_{11}$ | 235-237 |
| 16 | iso $C_3H_7$ | H | $-N(COCH_3)(\text{neo } C_5H_{11})$ | 135-136 |
| 17 | $CH_3$ | H | $-SCH_3$ | 207 |
| 18 | iso $C_3H_7$ | H | $-SCH_3$ | 178-179 |
| 19 | sec $C_4H_9$ | H | $-SCH_3$ | 148-149 |

For convenience in reference it is noted that the numbering of the thiatriazine ring used in this specification is as shown in the following formula:

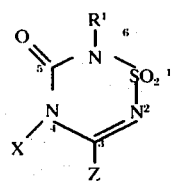

Where the group X in the formula previously set forth in this specification represents a hydrogen atom, the compounds of the invention may be capable of existing in two tautomeric forms which are in dynamic equilibrium with one another, as shown for example in the following scheme:

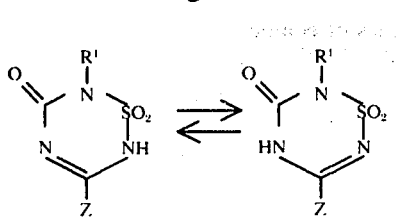

The relative proportion of each form may depend upon the particular compound in question, and upon such factors as the presence of a solvent and upon the ambient temperature. For convenience, when referring to a compound wherein X is hydrogen, only one structural formula may be given in the rest of this specification, although it is to be understood that this formula is also intended to include any proportion of the tautomeric form which may be present in a sample of the compound in question.

In another aspect, the invention provides methods of preparing compounds of the formula (I)

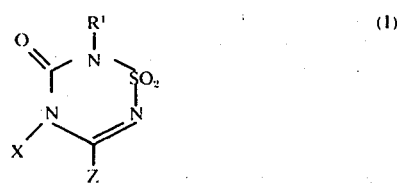

wherein $R^1$, X and Z are as hereinbefore defined.

Compounds of the last foregoing formula wherein X is hydrogen and Z is the group $R^2S$— may be prepared by the following reaction scheme A:

Scheme A

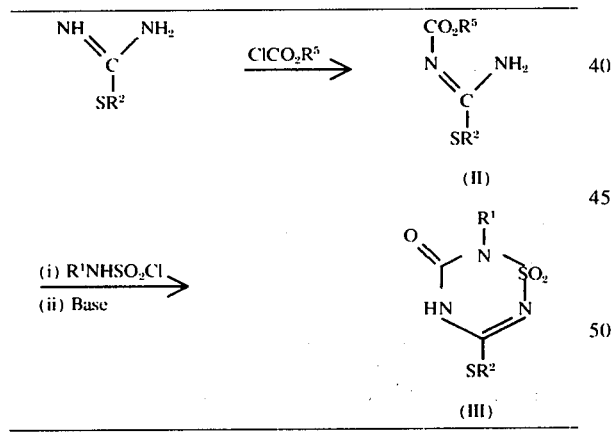

In the foregoing Scheme A, $R^1$ and $R^2$ have the meanings previously assigned to them, while $R^5$ represents an aliphatic radical, for example an alkyl radical of from 1 to 4 carbon atoms. The S-substituted isothioureas required as starting materials in this scheme are known compounds. The intermediates (II) can also be obtained by the following reaction scheme:

In the latter scheme, $R^2$ and $R^5$ have the meanings previously assigned to them while Hal represents chlorine, bromine, or codine.

Compounds according to the invention wherein X represents an aliphatic radical and Z represents an $R^2S$— group may be prepared by treating compounds of formula (III) above with an aliphatic sulphate ester or an aliphatic halide, in the presence of a base, for example an alkali metal alkoxide. In the case where the aliphatic group X is methyl, the reaction scheme is as follows:

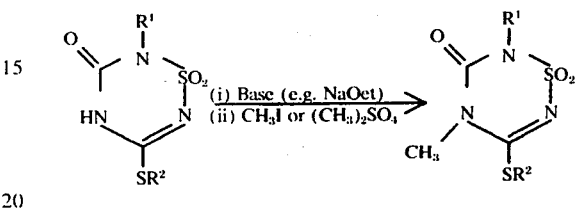

Compounds according to the invention wherein X is a hydrogen atom and Z represents an —$NR^3R^4$ group may be prepared by the following reaction Scheme B:

Scheme B

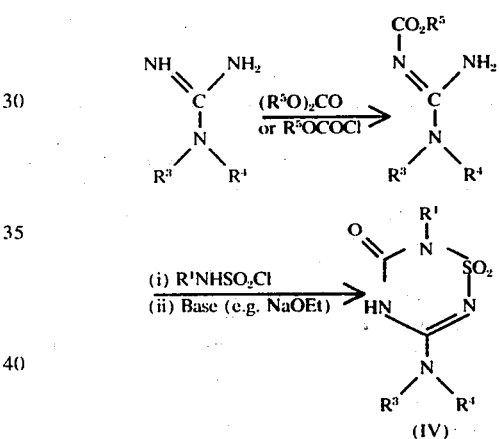

In Scheme B, the symbols $R^1$, $R^3$, $R^4$ and $R^5$ have the meanings previously assigned to them. The guanidine derivatives used as starting materials are known compounds. Compounds according to the invention wherein X is an aliphatic radical and Z is an —$NR^3R^4$ group may be prepared by treating compounds of Formula IV above with an aliphatic halide or an aliphatic sulphate ester, in the presence of a base, as shown in the following reaction scheme for the case where X is methyl.

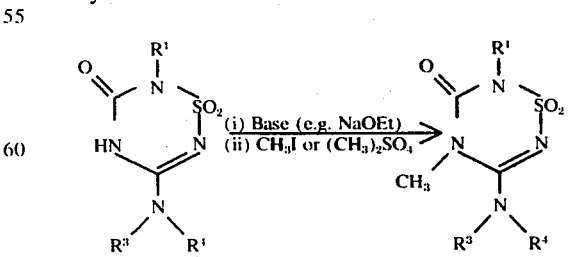

Alternatively, compounds according to the invention wherein X is an aliphatic radical and Z is an —$NR^3R^4$ group may be synthesised according to the method described in Scheme B above, using suitably N-substituted guanidine derivatives of formula:

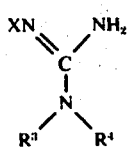

as starting material. The reaction scheme is illustrated below for the case where X is methyl and Z is —N(CH₃)₂.

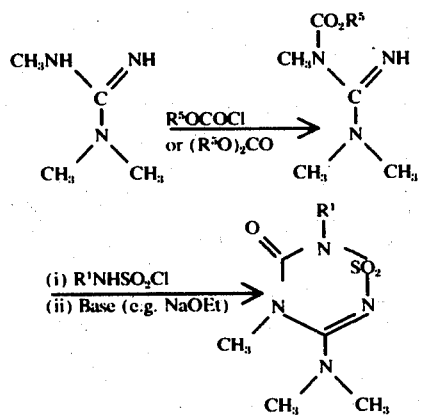

A still further method of preparing compounds according to the invention, wherein X is either hydrogen or an aliphatic radical and Z is an —NR³R⁴ group is to react the corresponding compounds in which Z is an R²S group with an amine R³R⁴NH as shown in Scheme C below:

Scheme C

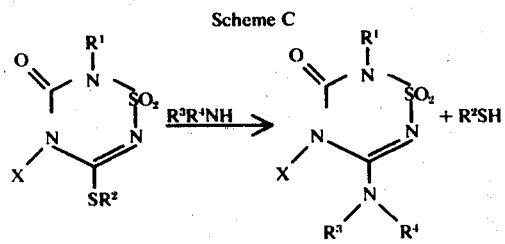

In Scheme C, X may be hydrogen or an aliphatic group, R³ may be hydrogen or an aliphatic radical, and R⁴ is an aliphatic radical, or the amine R³R⁴NH is a 5- or 6-membered heterocyclic amine, for example pyrrolidine or piperidine. Conveniently, the amine used in Scheme C is used in the form of a salt. Preferably the salt is a salt of a lower aliphatic carboxylic acid. Particularly preferred aliphatic carboxylic acids are alkanoic acids of 2 to 5 carbon atoms, for example acetic and propionic acids. The reaction may be carried out without a diluent by simply heating the amine salt with the thiosubstituted thiatriazine. Preferably the reaction temperature is from 100° to 200° C, for example 150° C.

Compounds according to the invention wherein R³ is a carboxylic acyl group may conveniently be prepared by acylating a compound according to the invention wherein Z is an —NHR⁴ group, according to methods well known for acylation of amines. The acylating agent may be a carboxylic acid chloride, for example acetyl or propionyl chloride, or an anhydride, for example acetic anhydride. Alternatively, compounds according to the invention wherein R³ is a carboxylic acyl group may be prepared by the reaction Scheme B set forth above in which a substituted guanidine is reacted with a sulphamoyl chloride in the presence of a base, using a guanidine derivative containing an R³ substituent which is an acyl radical.

In another aspect, the invention provides a process of severely damaging or killing unwanted plants, which comprises applying to plants, or to plant growth media, a severely damaging or killing amount of a compound of the formula

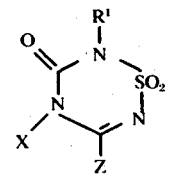

wherein R¹, X, and Z are as hereinbefore defined, or a salt thereof. The rate at which the compound is applied will depend upon a number of factors, for example, the identity of the plants to be severely damaged or killed, and the particular compound selected for use, but in general a rate of 0.1 to 10 kilograms per hectare is suitable, while from 0.5 to 5.0 kilograms per hectare is preferred.

The compounds of the invention are relatively less phytotoxic to cereal plants than they are towards many other plant species, and may therefore be used selectively to control the growth of weeds in cereal crops.

In another aspect, therefore, the invention provides a process of controlling the growth of weeds in cereal crops, which comprises applying to the crop area a compound of the formula:

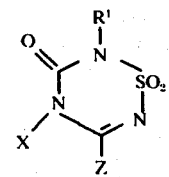

wherein R¹, X, and Z are as hereinbefore defined, or a salt thereof, in an amount sufficient to kill or severely damage weeds but insufficient to damage the crop substantially. The amount of compound applied will depend upon the crop and the weed species to be controlled, but as a general indication an amount of from 0.5 to 4 kilograms per hectare is often suitable. The skilled worker in the art will readily establish suitable rates of application by the application of known procedures.

A particular example of a cereal crop in which the compounds of the invention may be applied to control weeds is rice.

A particularly preferred group of compounds according to the invention for use as herbicides is the group of compounds in which the group Z is an amino group —NR³R⁴ in which the groups R³ and R⁴ are alkyl groups, preferably methyl groups. Especially preferred are compounds wherein Z is an —NR³R⁴ group wherein $R^3$ and $R^4$ are alkyl groups and $R^1$ is an isopropyl group.

The compounds of the invention have also been found to have activity against plant fungal diseases. In taking advantage of these fungicidal properties, it is of course necessary to apply the compounds to plants at rates below those at which significant herbicidal damage occurs.

In another aspect, therefore, the invention provides a process for combating fungal infections of plants, which comprises applying to the plants a fungicidally effective but non-phytotoxic amount of a thiatriazine derivative of the formula:

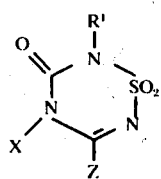

or a salt thereof, wherein $R^1$, X, and Z are as hereinbefore defined.

Preferred compounds for use in combating fungal infections are those of the last foregoing formula wherein $R^1$ is an alkyl group of 3 to 4 carbon atoms, X is a methyl radical, and Z is an $NR^3R^4$ group in which $R^3$ is hydrogen or alkyl of 1 to 3 carbon atoms and $R^4$ is alkyl of 1 to 3 carbon atoms. Particularly preferred compounds are compounds 11 and 13 of Table I.

The amount of the compound applied as a fungicide will vary, depending for example upon the fungal species to be controlled, the susceptibility of the host plant to damage by the particular compound employed, but in general a concentration of from 25 to 500 parts per million may be used.

Examples of fungal diseases which may be combated by application of compounds according to the invention include wheat rust (*Puccinia recondita*) and powdery mildew of barley and wheat (*Erisyphe graminis*). The compounds used in the process of killing or severely damaging plants or in combating fungal infestations of plants are preferably applied in the form of a composition in which the active ingredient is applied in admixture with a diluent or carrier. Preferably the composition also comprises a surface-active agent to assist in spreading the composition over the surface of plants to which it is applied.

Compositions according to the invention may be solid or liquid, and include both dilute compositions which are ready for immediate use, and concentrated compositions which require to be diluted before use. Preferably the compositions contain from 0.01 to 90% by weight of the thiatriazine used as active ingredient. Dilute compositions ready for use preferably contain from 0.01 to 2% of active ingredient, while concentrated compositions may contain from 20 to 90% of active ingredient, although from 20 to 70% is usually preferred.

Solid compositions may be in the form of a powder, in which the active ingredient is mixed with a powdered solid diluent. Suitable solid diluents include for example, Fuller's earth, powdered kaolin, gypsum, chalk and kieselguhr. Such solid compositions may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Examples of surface-active agents which may be used in the compositions of the invention include the products of condensation of ethylene oxide with the following substances: alkyl substituted phenols such as octyl phenol and nonylphenol; sorbitan monolaurate; oleyl alcohol; and propylene oxide polymer. A particular example of such a condensation product is the substance sold under the name of "Lissapol" (Lissapol is a Trade Mark). Other examples of surface-active agents include calcium dodecylbenzenesulphonate, and calcium, sodium, and ammonium lignosulphonates.

A preferred form of concentrated composition comprises the active ingredient which has been finely divided and which has been dispersed in water in the presence of a surface-active agent and a suspending agent. Preferred suspending agents are those which impart thixotropic properties to, and increaase the viscosity of, the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol. The invention is illustrated by the following Examples. In the Examples, all temperatures are in degrees Centigrade and all parts by weight unless otherwise stated.

EXAMPLE 1

This Example illustrates the preparation of 6-n-butyl-3-diethylamino-1,2,4,6-thiatriazin-5-one-1,1,-dioxide (Compound No. 4 of Table 1).

a. Preparation of $N^1$-diethyl-$N^2$-ethoxycarbonyl guanidine.

N,N-Diethylguanidine hydrochloride was added to a solution of 2 molar proportions of sodium hydroxide in water and kept at $-10°$ to $-5°$ C while ethyl chloroformate (1 molar proportion) was added over a period of 45 minutes. The solution was then allowed to warm to room temperature, evaporated in a vacuum, and the residue extracted with boiling chloroform. The chloroform extracts were evaporated and the residue recrystallised from a 4:1 mixture of ether and petroleum to give the product having a melting point of 72°–73° C.

b. To a suspension of the guanidinocarbamate from paragraph (a) above (11.2 g) in anhydrous tetrahydrofuran (50 ml) containing triethylamine (6 g) maintained at $-60°$ C was added dropwise and with stirring n-butyl sulphamoyl chloride (9.52 g). Following the exothermic reaction the mixture was then allowed to reach ambient temperature, when the solution was filtered. Evaporation of the filtrate gave a mobile oil comprising $N^1$-butylsulphamoyl-$N^2$-diethyl-$N^3$-ethoxycarbonyl guanidine, which was taken up in a solution of sodium (1.38 g) in anhydrous ethanol (25 ml) and the whole heated under reflux for 18 hours. The solvent was removed under reduced pressure and water (100 ml) was added. The mixture was extracted with chloroform (30 ml). The aqueous layer was acidified with HCl to pH 4 and re-extracted with chloroform (3×30 ml). The chloroform extracts were combined, dried with sodium sulphate, and evaporated. The residue was crystallised from chloroform-light petroleum to give the product (2.3 g) as colourless needles m.p. 142° C.

EXAMPLE 2

Following the method of Example 1, compounds Nos. 1, 2 and 3 of Table 1 were prepared. The guanidino carbamate intermediate required was prepared from N,N-dimethyl guanidine as described for the intermediate derived from N,N-diethylguanidine in paragraph (a) of Example 1. The $N^1$-dimethyl-$N^2$-ethoxycarbonyl guanidine so prepared had a melting point of 73°–76° C.

The sulphamoyl chlorides $R^1NHSO_2Cl$ required for preparation of compounds 1, 2 and 3 of Table 1 are all known compounds.

EXAMPLE 3

This example illustrates the preparation of compound No. 17 of Table 1. The preparation of this compound was carried out in a similar manner to the preparation described in paragraph (b) of Example 1, but using as starting materials N-methoxycarbonyl-S-methylisothiourea (5.92 g) having the structural formula

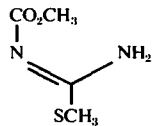

together with methylsulphamoyl chloride (5.18 g) and triethylamine. After the stage of heating under reflux with 1 molar proportion of sodium in anhydrous ethanol, the solvent was removed under reduced pressure and the residue taken up in water. The solution was brought to pH5 with glacial acetic acid and the precipitated solid recrystallised from ethanol-water to give the product (2.2 g) having a melting point of 207° C The N-methoxycarbonyl-S-methylisothiourea used as starting material is a known compound.

EXAMPLE 4

This Example illustrates the preparation of compound no. 6 of Table I.

a. Preparation of 6-isopropyl-3-methylthio-1,2,4,6-thiatriazin-5-one-1,1-dioxide Isopropylsulphamoyl chloride (39.4 g, 0.25 mole) was added dropwise and with stirring over a period of 10 minutes, to a solution of N-methoxycarbonyl-S-methylisothiourea (74 g, 0.5 mole) in anhydrous tetrahydrofuran (250 ml) maintained at −60°. The mixture was stirred at −60° for 45 minutes and then allowed to come to room temperature, whereupon it was stirred for another 2 hours. The solution was filtered, the filtrate evaporated, and water (200 ml) added to the oily residue. The solid so obtained was recrystallised from aqueous ethanol to give the ester of the following formula:

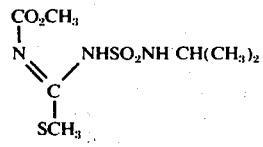

as colourless needles, (45.2 g) having a melting point of 97°. This ester (45.2 g) was dissolved in water (250 ml) containing sodium hydroxide (13.4 g) and the solution kept overnight at room temperature. The solution then acidified to pH3 with hydrochloric acid. The separated solid was recrystallised from a mixture of chloroform and light petroleum as colourless needles (34.7 g) having a melting point of 178°–179°.

b. Preparation of 6-isopropyl-4-methyl-3-methylthio-1,2,4,6-thiatriazin-5-one-1,1-dioxide A solution of the thiatriazinone prepared in (a) above (11.85 g) in methanol (75 ml) in which sodium (1.15 g) had been dissolved was evaporated to dryness. The residue was dissolved in acetonitrile (100 ml) containing methyl iodide (7.1 g) and the mixture was heated under reflux for 22 hours. The acetonitrile was removed under reduced pressure, the residue triturated with water, and the solid product collected. Crystallisation from chloroform-light petroleum gave the 4-methyl dirivative (11.1 g) having a melting point of 99°. The nuclear magnetic resonance spectrum and mass spectrum were in accord with methylation exclusively at the 4-position.

c. Preparation of compound no. 6

A mixture of 4-methyl derivative prepared in (b) above (2.51 g) and dimethylammonium acetate (5.25 g) was fused at 150° for 2 hours. Water (40 ml) was added to the cooled mixture and the solution extracted with chloroform (3 × 20 ml). The dried chloroform extracts were evaporated and the residue crystallised from chloroform-light petroleum to give compound no. 6 as colourless needles (1.4 g) having a melting point of 95°.

EXAMPLE 5

This example illustrates the preparation of compound no. 14 of Table I.

6-sec-Butyl-3-n-propylamino-1,2,4,6-thiatriazin-5-one-1,1-dioxide, prepared in the same way as described for compound no. 6 in Example 4, was heated under reflux in an excess of acetic anhydride for 3.5 hours. The acetic anhydride was removed under reduced pressure and the residue crystallised from n-hexane to give the product having a melting point of 87°–88°.

EXAMPLE 6

This example illustrates the herbicidal properties of compounds according to the invention.

Each compound (0.12 g) was mixed with 5 ml of an emulsion prepared by diluting 100 ml of a solution containing 21.8 grams per liter of Span 80 and 78.2 grams per liter of Tween 20 of methylcyclohexanone to 500 ml with water. Span 80 is a Trade Mark for a surface-active agent comprising sorbitan monolaurate. Tween 20 is a Trade Mark for a surface-active agent comprising a condensate of sorbitan monolaurate with 20 molar proportions of ethylene oxide. The mixture of the compound and the emulsion was shaken with glass beads and then diluted to 12 ml with water.

The spray composition so prepared was sprayed onto young pot plants (post-emergence test) of the species named in Table II below, at a rate equivalent to 1000 litres per hectare (10 kilograms of thiatriazine compound per hectare). Damage to plants was assessed 14 days after spraying by comparison with untreated plants, on a scale of 0 to 3 where 0 is 0–25% damage and 3 represents 75 to 100% kill. In a test for pre-emergence herbicidal activity, seeds of the test species were placed on the surface of fibre trays of soil and were sprayed with the compositions at the rate of 1000 liters per hectare. The seeds were then covered with further soil. Fourteen days after spraying, the seedlings in the sprayed fibre trays were compared with the seedlings in unsprayed control trays, the damage being assessed on the same scale of 0 to 3. The results are given in Table II below. For comparison, a commercially available herbicide sold under the name "Bentazon" and having the following structure:

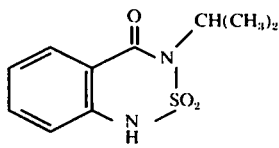

was included in the test.

TABLE II

| Compound No | Time of Appln | Test Plants | | | | | |
|---|---|---|---|---|---|---|---|
| | | Le | To | Cl | Wh | Dg | Pr |
| Bentazon | Pre | 0 | 0 | 0 | 0 | 0 | 0 |
| | Post | 3 | 3 | 2 | 0 | 0 | 1 |
| 1 | Pre | 0 | 0 | 3 | 0 | 1 | 0 |
| | Post | 0 | 0 | 0 | 0 | 0 | 0 |
| 2 | Pre | 0 | 0 | 0 | 0 | 0 | 0 |
| | Post | 3 | 3 | 2 | 0 | 2 | 2 |
| 3 | Pre | 0 | 0 | 0 | 0 | 0 | 0 |
| | Post | 3 | 3 | 3 | 0 | 0 | 0 |
| 5 | Pre | 3 | 0 | 0 | 0 | 0 | 0 |
| | Post | 3 | 3 | 3 | 0 | 0 | 0 |

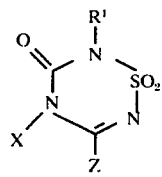

The names of the test species were as follows:

| Le | Lettuce |
| To | Tomato |
| Cl | Red Clover |
| Wh | Wheat |
| Dg | *Digitaria sanguinalis* |
| Pr | *Lolium perene* |

EXAMPLE 7

This Example illustrates the herbicidal activity of additional compounds according to the invention. Tests were carried out at an application rate of 10 kilograms per hectare as described in Example 6. The results are given in Table III below. They are on a scale of 0 to 3 as described in Example 6.

TABLE III

| Compound No. | Time of Applic'n | Test Plants | | | | | |
|---|---|---|---|---|---|---|---|
| | | Le | To | Cl | Wh | Dg | Pr |
| 6 | Pre | 1 | 1 | 1 | 1 | 2 | 0 |
| | Post | 3 | 3 | 3 | 0 | 1 | 1 |
| 7 | Pre | 0 | 0 | 1 | 0 | 0 | 0 |
| | Post | 3 | 3 | 3 | 0 | 1 | 1 |
| 8 | Pre | 0 | 0 | 0 | 0 | 0 | 0 |
| | Post | 1 | 1 | 2 | 0 | 2 | 0 |
| 9 | Pre | 0 | 0 | 0 | 0 | 0 | 0 |
| | Post | 0 | 1 | 2 | 0 | 1 | 0 |
| 10 | Pre | 0 | 0 | 0 | 1 | 1 | 0 |
| | Post | 3 | 3 | 2 | 1 | 1 | 0 |
| 11 | Pre | 1 | 1 | 0 | 0 | 1 | 0 |
| | Post | 3 | 3 | 3 | 1 | 0 | 0 |
| 12 | Pre | 1 | 1 | 1 | 0 | 2 | 0 |
| | Post | 3 | 3 | 3 | 1 | 1 | 0 |
| 13 | Pre | 1 | 1 | 1 | 0 | 1 | 0 |
| | Post | 3 | 3 | 3 | 2 | 1 | 1 |
| 14 | Pre | 3 | 0 | 3 | 0 | 3 | 0 |
| | Post | 1 | 3 | 1 | 0 | 3 | 0 |
| 17 | Pre | 0 | 0 | 0 | 0 | 3 | 0 |
| | Post | 3 | 3 | 3 | 0 | 0 | 0 |
| 18 | Pre | 2 | 2 | 1 | 0 | 0 | 0 |
| | Post | 3 | 1 | 1 | 0 | 0 | 0 |
| 19 | Pre | 0 | 0 | 0 | 0 | 0 | 0 |
| | Post | 3 | 3 | 1 | 0 | 2 | 0 |

EXAMPLE 8

This Example illustrates the herbicidal properties of compounds according to the invention in tests in which the compounds were applied to a further range of test plants. The tests were carried out as described in Example 6, but using various application rates. The damage to the plants was assessed on a scale of 0 to 5 where 0 is 0 to 20% damage and 5 is complete kill. The results are collected in Table IV.

TABLE IV

| Compnd No. | Rate of Applic. Kg/ha | Time of Applic. | TEST PLANTS | | | | | | | | | | | | | | | | |
|---|---|---|---|---|---|---|---|---|---|---|---|---|---|---|---|---|---|---|---|
| | | | Sb | Rp | Ct | P | Sn | Ip | Am | Pa | Ca | Po | Mz | Br | Rc | Ot | Dg | Ei | Pn |
| 2 | 1 | Pre | 0 | 1 | 0 | 0 | 2 | 1 | 0 | 0 | 0 | 0 | 0 | 0 | 0 | 0 | 1 | 0 | 0 |
| | | Post | 0 | 2 | 1 | 0 | 3 | 3 | 3 | 2 | 4 | 4 | 0 | 0 | 0 | 0 | 1 | 1 | 0 |
| 3 | 5 | Post | 2 | 3 | 0 | 0 | 5 | 3 | 1 | 0 | 3 | 3 | 0 | 0 | 0 | 0 | 1 | 1 | 0 |
| 5 | 1 | Pre | 4 | 4 | 0 | 1 | 1 | 2 | 4 | 4 | 4 | 1 | 1 | 0 | 2 | 3 | 2 | 3 | — |
| | | Post | 3 | 4 | 1 | 2 | 4 | 3 | 4 | 4 | 5 | 5 | 0 | 0 | 0 | 2 | 3 | 3 | 4 |
| 6 | 5 | Pre | 5 | 4 | 3 | 3 | 5 | 4 | 5 | 5 | 4 | 5 | 1 | 2 | 0 | 3 | 5 | 5 | 4 |
| | | Post | 3 | 4 | 4 | 3 | 5 | 4 | 5 | 5 | 5 | 0 | 1 | 0 | 2 | 4 | 3 | 4 | |
| 6 | 1 | Pre | 4 | 3 | 0 | 1 | 5 | 3 | 4 | 5 | 3 | 4 | 0 | 0 | 0 | 3 | 3 | 3 | 3 |
| | | Post | 3 | 4 | 2 | 1 | 4 | 4 | 5 | 4 | 5 | 5 | 0 | 0 | 0 | 1 | 1 | 0 | 4 |
| 7 | 5 | Pre | 5 | 4 | 3 | 3 | 5 | 4 | 4 | 5 | 4 | 4 | 0 | 1 | 0 | 4 | 4 | 4 | 3 |
| | | Post | 4 | 4 | 4 | 3 | 5 | 4 | 5 | 5 | 5 | 0 | 1 | 1 | 1 | 3 | 2 | 4 | |
| 11 | 5 | Pre | 4 | 3 | 1 | 1 | 4 | 4 | 4 | 2 | 4 | 0 | 0 | — | 0 | 2 | 0 | 1 | |
| | | Post | 3 | 4 | 0 | 1 | 3 | 4 | 4 | 3 | 4 | 4 | 0 | 0 | 1 | 0 | 2 | 3 | — |
| 12 | 5 | Pre | 4 | 4 | 1 | 0 | 4 | 1 | 4 | 5 | 4 | 5 | 2 | 1 | 0 | 2 | 3 | 0 | 0 |
| | | Post | 3 | 4 | 0 | 2 | 4 | 4 | 5 | 4 | 4 | 5 | 0 | 1 | 0 | 1 | 3 | 4 | — |
| 13 | 5 | Pre | 5 | 4 | 1 | 0 | 5 | 4 | 4 | 3 | 4 | 0 | 2 | — | 2 | 2 | 1 | 2 | |
| | | Post | 4 | 5 | 3 | 1 | 5 | 5 | 5 | 3 | 4 | 5 | 0 | 1 | 1 | 0 | 2 | 4 | — |
| 17 | 5 | Pre | 2 | 1 | 0 | 0 | 0 | 0 | 0 | 0 | 0 | 1 | 0 | 0 | 0 | 0 | 1 | 4 | 0 |

TABLE IV-continued

| Compnd No. | Rate of Applic. Kg/ha | Time of Applic. | Sb | Rp | Ct | P | Sn | Ip | Am | Pa | Ca | Po | Mz | Br | Rc | Ot | Dg | Ei | Pn |
|---|---|---|---|---|---|---|---|---|---|---|---|---|---|---|---|---|---|---|---|
| | | Post | 4 | 4 | 1 | 3 | 5 | 4 | 4 | 4 | 5 | 3 | 0 | 0 | 0 | 0 | 0 | 0 | 1 |

A dash (—) means that no test was carried out.

The names of the test plants are as follows:

| | |
|---|---|
| Sb - Sugar beet | Ca - *Chenopodium album* |
| Rp - Rape | Po - *Portulaca oleracea* |
| Ct - Cotton | Mz - Maize |
| P - Pea | Br - Barley |
| Sn - *Senecio vulgaris* | Rc - Rice |
| Ip - *Ipomoea purpurea* | Ot - Oat |
| Am - *Amaranthus retroflexus* | Dg - *Digitaria sanguinalis* |
| Pa - *Polygonum aviculare* | Ei - *Eleusine indica* |
| | Pn - *Poa annua* |

EXAMPLE 9

This example illustrates the herbicidal activity of compound no. 6 of Table I against a further range of plant species. Tests were carried out as described in Example 6, but with a small variation of the pre-emergence test procedure. In the pre-emergence test, the seeds of the test plants were sown in shallow grooves in soil contained in fibre trays. The seeds were then covered with a layer of soil, and the test compound sprayed on the soil surface. Finally the sprayed surface was covered with a further thin layer of soil. The damage to the plants was assessed after 3 weeks in the pre-emergence test and 2 weeks in the post-emergence, on a scale of 0 to 9 where 0 is 0 to 11% damage and 9 is complete kill.

The results are given in Table V.

TABLE V

| Time of Applic. | Rate of Applic | Ei | Ec | St | Dg | Po | Am |
|---|---|---|---|---|---|---|---|
| Pre | 1 | 6 | 7 | 8 | 7 | 9 | 7 |
| | 2 | 8 | 7 | 8 | 7 | 9 | 9 |
| | 4 | 9 | 7 | 9 | 9 | 9 | 9 |
| Post | 1 | 2 | 3 | 2 | 2 | 9 | 9 |
| | 2 | 3 | 6 | 3 | 5 | 9 | 9 |
| | 4 | 6 | 8 | 3 | 9 | 9 | 9 |

Test Species

Ei - *Eleusine indica*
Ec - *Echinochloa crus-galli*
St - *Setaria viridis*
Dg - *Digitaria sanguinalis*
Po - *Portulaca oleracea*
Am - *Amaranthus retroflexus*

EXAMPLE 10

This Example illustrates the fungicidal properties of compounds according to the invention. The compounds were tested against foliar fungal diseases of plants. In the tests, a composition comprising an aqueous solution or suspension containing 200 parts per million of the test compound was sprayed on to the foliage of uninfected plants. The plants were then exposed to infection by the fungal diseases it was desired to control. After a period of days, depending upon the particular disease, the extent of the desease was assessed as a percentage of the amount of the disease occurring on control plants treated in the same way as the test plants except that they were not sprayed with the compounds of the invention. The percentage amount of disease was graded as below:

| Grading | Percentage Amount of Disease |
|---|---|
| 0 | 61 to 100 |
| 1 | 26 to 60 |
| 2 | 6 to 25 |
| 3 | 0 to 5 |
| 4 | No disease |

In Table VI below the name of the disease is given in the first column, and the second column gives the time which was allowed to pass between exposing the plants to infection and assessing the amount of disease.

| Disease and Plant | Time Interval (days) | Disease Code Letter |
|---|---|---|
| *Puccinia recondita* (wheat rust) | 10 | A |
| *Erisiphe graminis* (powdery mildew of wheat) | 10 | B |
| *Plasmopara viticola* downey mildew of vine) | 10 | C |

The results of the tests are given in Table VII below. A dash (-) means no test was performed. A letter P means that some degree of damage to the plant was observed.

TABLE VII

| Compound No. (Table I) | Disease Code Letter | | |
|---|---|---|---|
| | A | B | C |
| 1* | 2 | — | — |
| 2* | 0 | 1 | — |
| 3 | 0 | — | 3 |
| 6 | 4P | — | 4P |
| 7 | 4P | — | 4P |
| 10 | 0 | 0 | 4P |
| 11 | 3P | 4P | 4P |
| 12 | 2 | 3P | 4P |
| 13 | 3P | 4P | 4 |
| 19 | 0 | 1 | 1 |

*Tested at 100 parts per million

I claim:

1. A process of severely damaging or killing unwanted plants, which comprises applying to the locus area an effective amount of a thiatriazine compound of the formula

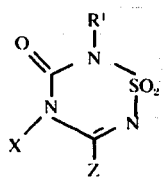

and salts thereof, wherein $R^1$ is cyclohexyl or an alkyl radical of up to 8 carbon atoms; X is a hydrogen atom or an alkyl group of 1 to 3 carbon atoms; and Z is a group $R^2S-$ wherein $R^2$ is an alkyl group of 1 to 4 carbon atoms, or Z is a group $-NR^3R^4$ wherein $R^3$ is a hydrogen atom, an alkyl radical of 1 to 5 carbon atoms, or an alkanoyl radical of 2 to 5 carbon atoms, and $R^4$ is an alkyl radical of 1 to 5 carbon atoms.

2. A process according to claim 1 wherein the thiatriazine compound is applied at the rate of from 0.1 to 10 kilograms per hectare.

3. A process of controlling the growth of weeds in cereal crops, which comprises applying to the crop area a thiatriazine compound of the formula

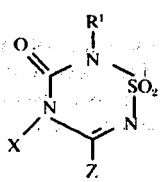

and salts thereof, wherein $R^1$ is cyclohexyl or an alkyl radical of up to 8 carbon atoms; X is a hydrogen atom or an alkyl group of 1 to 3 carbon atoms; and Z is a group $R^2S-$ wherein $R^2$ is an alkyl group of 1 to 4 carbon atoms, or Z is a group $-NR^3R^4$ wherein $R^3$ is a hydrogen atom, an alkyl radical of 1 to 5 carbon atoms, or an alkanoyl radical of 2 to 5 carbon atoms, and $R^4$ is an alkyl radical of 1 to 5 carbon atoms, said compound being applied in an amount sufficient to kill or severely damage weeds, but insufficient to damage the crop substantially.

4. A process according to claim 3 in which the cereal crop is rice.

5. A process according to claim 3 in which the thiatriazine derivative is applied at the rate of 0.5 to 4 kilograms per hectare.

6. A process for killing undesired plants which comprises applying to the locus of said plants an effective amount of a compound of the formula:

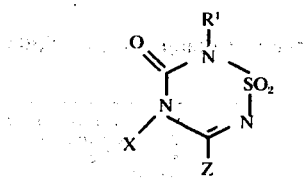

and salts thereof, wherein $R^1$ is cyclohexyl or an alkyl radical of up to 8 carbon atoms; X is a hydrogen atom or an alkyl group of 1 to 3 carbon atoms; and Z is a group $R^2S-$ wherein $R^2$ is an alkyl group of 1 to 4 carbon atoms, or Z is a group $-NR^3R^4$ wherein $R^3$ is a hydrogen atom, an alkyl radical of 1 to 5 carbon atoms, or an alkanoyl radical of 2 to 5 carbon atoms, and $R^4$ is an alkyl radical of 1 to 5 carbon atoms.

7. The process of claim 6 wherein $R^1$ is methyl, n-butyl, sec-butyl, cyclohexyl or iso-propyl; X is hydrogen or methyl; and Z is $-N(CH_3)_2$, $-N(C_2H_5)_2$, $-NHCH_3$,

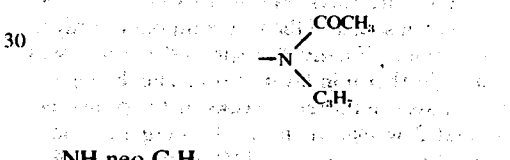

$-NH$ neo $C_5H_{11}$,

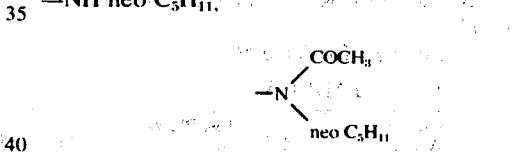

or $-SCH_3$.

8. The process of claim 6 wherein $R^1$ is alkyl of 1 to 8 carbon atoms or cyclohexyl; X is hydrogen or alkyl of 1 to 3 carbon atoms; and Z is a group $R^2S-$ wherein $R^2$ is alkyl of 1 to 4 carbon atoms or Z is a group $-NR^3R^4$ wherein $R^3$ is hydrogen, alkyl of 1 to 5 carbon atoms or $-COCH_3$ and $R^4$ is alkyl of 1 to 5 carbon atoms.

* * * * *